(12) United States Patent
Abramowitz et al.

(10) Patent No.: US 7,135,465 B2
(45) Date of Patent: Nov. 14, 2006

(54) SUSTAINED RELEASE BEADLETS CONTAINING STAVUDINE

(75) Inventors: Robert Abramowitz, West Windsor, NJ (US); Denise M. O'Donoghue, Hightstown, NJ (US); Nemichand B. Jain, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 691 days.

(21) Appl. No.: 09/821,103

(22) Filed: Mar. 29, 2001

(65) Prior Publication Data

US 2002/0002147 A1 Jan. 3, 2002

Related U.S. Application Data

(60) Provisional application No. 60/193,588, filed on Mar. 30, 2000.

(51) Int. Cl.
*A61K 31/70* (2006.01)
*A61K 9/16* (2006.01)

(52) U.S. Cl. .................. 514/50; 424/57; 424/61; 424/451

(58) Field of Classification Search ............... 514/50; 424/57, 61, 451
See application file for complete search history.

(56) References Cited

U.S. PATENT DOCUMENTS

| | | | |
|---|---|---|---|
| 4,670,270 A | 6/1987 | Germino et al. .......... 426/89 |
| 4,671,963 A | 6/1987 | Germino et al. .......... 426/89 |
| 4,917,900 A * | 4/1990 | Jones et al. ............ 424/493 |
| 4,940,556 A | 7/1990 | MacFarlane et al. ....... 264/15 |
| 4,978,655 A * | 12/1990 | Lin et al. ................ 514/50 |
| 5,478,574 A | 12/1995 | Baichwal et al. ......... 424/485 |
| 5,691,372 A | 11/1997 | Tung et al. ............. 514/452 |
| 5,709,885 A | 1/1998 | Hellén et al. .......... 424/489 |
| 5,723,452 A | 3/1998 | Chan .................... 514/155 |
| 5,723,490 A | 3/1998 | Tung .................... 514/478 |
| 5,725,886 A | 3/1998 | Erkoboni et al. ........ 424/499 |
| 5,766,623 A | 6/1998 | Ayres et al. ............ 424/441 |
| 5,780,055 A | 7/1998 | Habib et al. ............ 424/464 |
| 5,849,911 A | 12/1998 | Fassler et al. .......... 544/335 |
| 5,869,097 A | 2/1999 | Wong et al. ............ 424/473 |
| 5,883,252 A | 3/1999 | Tung et al. ............. 544/71 |
| 5,904,937 A | 5/1999 | Augello et al. .......... 424/494 |
| 5,905,068 A | 5/1999 | Chen et al. ............. 514/19 |
| 5,914,332 A | 6/1999 | Sham et al. ............ 514/274 |
| 5,919,776 A | 7/1999 | Hagmann et al. ......... 514/159 |
| 5,935,597 A | 8/1999 | Visser ................. 424/449 |
| 5,945,413 A | 8/1999 | Tung et al. ............ 514/193 |
| 5,955,485 A | 9/1999 | DeBrabander et al. .... 514/366 |
| 5,962,462 A | 10/1999 | Mills et al. ........... 514/278 |
| 5,990,155 A | 11/1999 | Tung et al. ............ 514/456 |
| 6,013,644 A | 1/2000 | Mills et al. ......... 514/210.16 |
| 6,093,743 A | 7/2000 | Lai et al. ............. 514/599 |
| 6,110,498 A | 8/2000 | Rudnic et al. .......... 424/473 |
| 6,110,946 A | 8/2000 | Fassler et al. ......... 514/333 |
| 6,120,803 A | 9/2000 | Wong et al. ............ 424/473 |
| 6,124,319 A | 9/2000 | MacCoss et al. ......... 514/318 |
| 6,127,372 A | 10/2000 | Tung et al. .......... 514/253.11 |
| 6,132,771 A | 10/2000 | Depui et al. ........... 424/468 |
| 6,136,827 A | 10/2000 | Caldwell et al. ........ 514/329 |
| 6,136,835 A | 10/2000 | Camden ................ 514/383 |
| 6,140,349 A | 10/2000 | Caldwell et al. ........ 514/326 |
| 6,166,004 A | 12/2000 | Fassler et al. ......... 514/188 |
| 6,166,037 A | 12/2000 | Budhu et al. .......... 514/326 |
| 6,172,061 B1 | 1/2001 | Nishimura et al. ..... 514/231.5 |
| 6,177,460 B1 | 1/2001 | Camden ................ 514/485 |
| 6,180,634 B1 | 1/2001 | Vacca et al. ......... 514/254.11 |
| 6,194,391 B1 | 2/2001 | Schinazi et al. .......... 514/50 |
| 6,194,430 B1 | 2/2001 | Camden et al. .......... 514/303 |
| 6,607,747 B1 * | 8/2003 | Ullah et al. ........... 424/451 |
| 6,692,767 B1 * | 2/2004 | Burnside et al. ........ 424/489 |

OTHER PUBLICATIONS

Abrahamsson, B. et al., "Gastro-intestinal transit of a multiple-unit formulation (metoprolol CR/ZOK) and a non-disintegrating tablet with the emphasis on colon" *International Journal of Pharmaceutics*, 140, p. 229-235 (1996).

* cited by examiner

*Primary Examiner*—Leigh C. Maier
(74) *Attorney, Agent, or Firm*—Scott Alexander McNeil; Warren K. Volles; Pamela A. Mingo

(57) ABSTRACT

Extended dosage forms of stavudine are provided comprising beadlets formed by extrusion-spheronization and coated with a seal coating. The beadlets are also coated with a modified release coating such that a hard gelatin capsule containing such beadlets will provide blood levels of stavudine over approximately 24 hours. The beadlets are prepared from a dry blend of stavudine, a spheronizing agent, a suitable diluent and a stabilizing amount of magnesium stearate. The magnesium stearate, in contrast to other similar pharmaceutical adjuncts, has been found to stabilize stavudine against degradation due to hydrolysis in the presence of the limited amount of water necessary for the extrusion-spheronization process. Also included in the scope of the invention are hard gelatin capsules containing, in addition to the stavudine beadlets, similar beadlets containing other therapeutic agents utilized to treat retroviral infections.

34 Claims, No Drawings

SUSTAINED RELEASE BEADLETS CONTAINING STAVUDINE

RELATED APPLICATIONS

This is a non-provisional application which claims the benefit of provisional application U.S. Ser. No. 60/193,588 filed Mar. 30, 2000.

BACKGROUND OF THE INVENTION

Stavudine (3'-deoxythymidin-2'-ene (3'-deoxy-2',3'-didehydrothymidine) is approved by the U.S. Food & Drug Administration for the therapeutic treatment of patients infected with retroviruses. The compound, a nucleoside reverse transcriptase inhibitor, and its preparation are disclosed, for example, in U.S. Pat. No. 4,978,655, issued Dec. 18, 1990. It is known that stavudine is effective in the treatment of infections caused by retroviruses such as murine leukemia virus and human immunodeficiency virus, i.e. HIV; HTLV III/LAV virus (the AIDS virus). Stavudine has enjoyed notable commercial success since its introduction.

In the treatment of HIV infections, it is common for the patient to receive a combination of medicaments. Hence, the patients typically have a very large daily pill burden. It will be appreciated that a reduction in the daily pill burden by even one pill may be significant in this patient population. Ultimately, the reduced pill burden may result in increased patient adherence to their HIV regimens, particularly for the drugs for which a once daily dosing can be implemented. Once daily dosing is important in terms of achieving enhanced patient compliance, improved sustained blood levels of medication, safety and patient convenience, hence patient acceptance.

It has been found in gamma scintigraphy studies that stavudine is well absorbed in the upper intestine. The absorption in the colon is approximately one half that of the small intestine. The optimal formulation would be designed to release approximately 40% of the stavudine in four hours and the remainder over the next twelve to twenty hours. A 100 mg. extended dosage form of stavudine, therefore, would be designed to have the same bioavailability as the commercial 40 mg. immediate release capsules given twice daily. Hence, those skilled in the art will appreciate that stavudine would be amenable to once daily dosing if a suitable extended release formulation could be developed. A problem in the formulation of a suitable extended dosage form of stavudine is its sensitivity to moisture that causes it to hydrolyze, primarily into thymine. This moisture sensitivity has not been a problem with the commercial non-sustained release dosage form of stavudine because it is a dry granulation that is filled into hard gelatin capsules. However, sustained release dosage forms conventionally require different compounding procedures typically including a granulation step involving an aqueous medium. Hence, medicaments that are moisture sensitive, such as stavudine, can present a significant challenge to attempts to formulate them. In accordance with the present invention, a method has been found whereby stavudine can be successfully compounded into an extended release formulation utilizing conventional techniques without appreciable loss of potency due to hydrolysis.

SUMMARY OF THE INVENTION

Stable beadlets containing stavudine prepared by conventional extrusion/spheronization techniques are provided. The beadlets are suitable for preparing extended release dosage forms capable of providing 24 hour blood levels of stavudine with a single dose. The beadlet formulation in accordance with the present invention is novel in that there is included in the dry blend an amount of magnesium stearate sufficient to stabilize stavudine against hydrolysis during subsequent processing to form the beadlets. Hydrolysis of stavudine in the formulation manifests itself both in loss of potency and as a discoloration of the beadlets formed therefrom, i.e. beadlets formed in accordance with the invention stay white whereas those prepared with other similar conventional adjuncts become yellow to brown in color. The beadlets are first seal-coated and then coated with a modified release coating of a polymeric barrier material, such as ethylcellulose, and a suitable plasticizer therefor that provides for the release of stavudine over time, so that they will provide blood levels of stavudine over approximately 24 hours. An appropriate amount of such beadlets is filled into conventional hard gelatin capsules. Similar beadlets of other compounds active against retroviruses may be included in the capsules as well, thereby providing for an extended combination therapy over approximately 24 hours.

DETAILED DESCRIPTION OF THE INVENTION

Studies of various conventional extended release dosage forms have shown that a beadlet formulation appears to be most suitable for stavudine. One of the primary reasons for this is that, as stated above, it is common for AIDS medications to be given in combinations in order to obtain the maximum antiretroviral effect. Utilizing beadlets, it is possible to compound two or more medications individually into beadlets, which are then filled into conventional hard gelatin capsules. Such separate compounding avoids any potential compounding problems that might be encountered with trying to combine such medications into the same formulation. Another reason favoring beadlets is that it has been found that stavudine is generally absorbed throughout the GIT as described above. Therefore, it would be ideally suited for extended release in a form, such as beadlets, that would slowly pass through the system. In addition, of the recognized forms of sustained or extended release, beadlets have been shown to possess a more reproducible GI transit time than larger dosage forms, such as tablets.

A significant advantage of an extended release dosage form of stavudine is that a single daily dosage tends to increase patient compliance since fewer doses are missed. This is particularly important with regard to AIDS medication since it is a primary objective of the therapy to keep the virus at low or undetectable levels. A further advantage of extended release dosage forms of medicaments such as stavudine is a reduction in the side effects resulting from the elevated blood levels that can result from ingesting individual dosages too close together. An additional advantage of the beadlets of the present invention over other extended forms of sustained release is that there is a lower incidence of dose dumping as might result, for example, from inadvertently chewing a matrix tablet. Finally, since many AIDS patients often experience GI upset or diarrhea, beadlets are a preferable dosage form since they pass more slowly through the small intestine and colon and thus produce more consistent blood levels. It is reported, for example, in the *Int.*

J. Pharm. Vol. 140 (AUG. 30), pages 229–235 (1996) that pellets have a longer residual time in the colon in comparison to tablets.

Those of ordinary skill in the art will recognize that there are several techniques for forming beadlets containing a medicament that can be coated to produce extended release. Drug coating or layering onto sugar seeds, and direct formulation by rotary granulation are two such conventional techniques. However, both of these methods would entail substantial contact with water, which would result in degradation of a medicament, such as stavudine, that hydrolyzes comparatively quickly in contact with moisture and heat. Other methodologies utilizing non-aqueous solvents might be utilized, but would be significantly disadvantaged due to safety and environmental issues. The extrusion and spheronization technique would therefore appear to be the method of choice since it permits the manufacture of beadlets containing a high loading of medicament in a relatively short time with, most important for stavudine, minimum contact with water.

Extrusion spheronization is a well-known technique for forming beadlets of medicament. The process, in essence, comprises forming a mixture of an art-recognized spheronizing agent and other suitable dry excipients with the medicament, wet granulating the mixture with a limited amount of water to form a wetted mass of powder that is extruded through a conventional extruder equipped with a suitable screen to form discrete extrudates. The extrudates are then transferred to a spheronizer wherein they are cut and shaped into discrete spherical beadlets, which are thereafter dried. Spheronizers are commercial equipment well known to those of ordinary skill in the art. The resulting spheroids may vary in both size and degree of sphericity depending on a number of factors such as the amount of water in the wetted powder, the configuration of the plates in the spheronizer, both the speed and duration of operation of the spheronizer, and the like. Typically, spheroids produced by this process are 0.5 to 1.5 millimeters at their largest dimension. Such spheroids are ideally suited for coating to form an extended release dosage form by virtue of their size and shape. For the same reason, they are also readily filled into conventional empty gelatin capsules. It will be appreciated that, with a moisture sensitive medicament such as stavudine, the steps of extrusion and spheronizing would be carried out in rapid succession to minimize contact with water.

While there are a number of spheronizing agents known to those of ordinary skill in the art utilized as being useful in the manufacture of beadlets by the extrusion/spheronization technique, the most common is microcrystalline cellulose. Other agents useful in extrusion/spheronization techniques include sodium carboxymethylcellulose and corn starch, however, the quality of beadlets prepared therefrom is not as good as those obtained utilizing microcrystalline cellulose. The spheronizing agent functions to provide plasticity to the formulation that fosters the formation of spherical beadlets and also to supply the binding properties that give the beadlets strength and integrity. Microcrystalline cellulose is typically utilized as the single excipient in spheronizing techniques or it may commonly be combined with a suitable diluent, typically lactose, more preferably Lactose Hydrous NF. Microcrystalline cellulose is commercially available from a number of sources and in a variety of grades and physical characteristics or specifications. For example, a variety of grades and types of microcrystalline cellulose are available under the trademark Avicel from FMC Corporation. Typically, microcrystalline cellulose, with or without a diluent such as lactose, is utilized to formulate the granulation for spheronization without any other conventional additives, such as conventional tabletting lubricants, flowing agents and the like. In fact, the manufacturer's descriptive literature on Avicel states that it is an advantage of the product that it can be used without such conventional agents. A description of the use of microcrystalline cellulose in extrusion and spheronization as well as a composition containing microcrystalline cellulose and a hydrocolloid may be found in U.S. Pat. No. 5,725,886, assigned to FMC Corporation.

Even the use of extrusion and spheronization techniques with a minimum contact with water has not proved ideal for formulation of extended dosage forms of stavudine due to its tendency to hydrolyze in the presence of moisture. However, it has been found in accordance with the present invention, that stavudine can be compounded into a granulation suitable for extrusion and spheronization without undergoing any material degradation by the inclusion in the formulation of magnesium stearate. This result is considered unexpected for two reasons. First, because of the properties of the excipients utilized to form such granulations, specifically microcrystalline cellulose, and the nature of the techniques itself, one of ordinary skill in the art would not be motivated to consider including a conventional tabletting lubricant in the formulation. Second, magnesium stearate is effective in stabilizing stavudine in the granulation whereas other similar conventional tabletting lubricants/processing aids, such as talc and colloidal amorphous silicon, do not produce the stabilizing effect. In general, an amount of magnesium stearate between about 0.5 and 3.0 percent by weight, preferably between about 1.4 and 1.7 percent by weight, based on the weight of stavudine present, is sufficient to provide the stabilizing effect realized in accordance with the present invention. Magnesium stearate possesses an added unexpected advantage in that it protects the beadlets from turning yellow to brown, i.e. beadlets prepared from a formulation containing magnesium stearate are noticeably whiter than those prepared from formulations without it or with other conventional tabletting lubricants.

In general, stavudine comprises from about 33 to about 67 percent by weight of the beadlets formed by extrusion and spheronization in accordance with the present invention. The process is advantageous in that it enables a high loading of medicament into the beadlets. The finished dosage forms will contain stavudine in various dosages depending of its projected therapeutic regimen. Generally, beadlets containing dosages of stavudine of 37.5 mg., 50 mg., 75 mg. and 100 mg., respectively, would be contemplated in a single hard gelatin capsule. The requisite amount of stavudine is combined with microcrystalline cellulose, a suitable diluent such as lactose, preferably Lactose Hydrous NF, and a stabilizing amount of magnesium stearate, thoroughly mixed and wet granulated with a minimum amount of water to achieve the requisite granulation. The diluent is required to obtain a reasonable weight for the beadlets so that they can be filled into conventional gelatin capsules utilizing conventional filling apparatus. It will be understood by those of ordinary skill in the art of pharmaceutical compounding that other similar ingredients may be substituted for the preferred lactose in the formulations. Such other diluents include, for example, dicalcium phosphate, mannitol and cornstarch. The granulation is formed in a conventional blender and is thereafter extruded utilizing a Nica, Luwa or other conventional extrusion equipment to form an extrudate which is then processed in conventional spheronizing equipment such as Caleva, Nica, Luwa, or other type, to convert the extrudate into beadlets of the desired particle size range. The beadlets contemplated in accordance with the present invention would be, for example, from about 0.7 to about 1 mm in diameter.

The beadlets thus-formed may be dried by tray drying in a suitable oven or by fluidized bed drying. The finished beadlets are coated with a seal coating utilizing conventional film-formers such as hydroxypropyl methylcellulose (HPMC), hydroxypropyl cellulose (HPC) and the like, in combination with an antiadherent agent to retard the tendency of the beadlets to agglomerate during the coating operation. While talc is preferred, microcrystalline cellulose and magnesium stearate may also serve as antiadherent agents. In general, the weight ratio of film-former to antiadherent agent in the coating composition will be from about 4:1 to 2:1. The seal coating aids in rounding the beadlets and insulates stavudine in the beadlets from contact with the modified release coating. The beadlets are then coated with a barrier or modified release coating to achieve extended dissolution and absorption over a period such that they will provide blood levels of stavudine over a 24 hour period. Typically, the modified release coating constitutes from about four to about six percent by weight of the finished beadlets. The modified release coating comprises a polymeric barrier material and a suitable plasticizer therefor. The polymeric barrier material may be a suitable polymethacrylate but is preferably a commercially available aqueous latex dispersion of ethylcellulose. Suitable commercial preparations of ethylcellulose include, e.g. Surelease available from Colorcon, which is available in combination with a plasticizer and Aquacoat® available from FMC Corporation, which is typically mixed with a suitable plasticizer. Preferred plasticizers include a mixture of acetylated monoglycerides, dibutyl sebacate, triethylcitrate and the like. An appropriate amount of the modified release coated beadlets is then filled into the appropriate size hard gelatin capsules. Generally, the coated beadlets will be comprised of from about 50 to about 67 percent by weight, preferably about 55 percent by weight, of stavudine.

A further advantage of the beadlets of the present invention is that they can be combined in hard gelatin capsules as described with other medicaments useful in the treatment of retroviral infections so that blood levels of the combination over a period of 24 hours can be achieved with a single dose. Such combination therapy is considered a treatment of choice in the treatment of AIDS. Such therapeutics agents include, for example, didanosine (2', 3'-dioxyinosine), [3S-(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl }-2,3,6,10,13-pentaazaretetradecanedioic acid dimethyl ester, indinavir, lodenosine and others as are or will hereafter become available for the treatment of retroviral infections. Such agents would be utilized in combinations of two or three as therapeutically appropriate and might be combinable in appropriate sized hard gelatin capsules. It is within the purview of the present invention to combine such antiretrovirals dosage-wise such that a two capsule dose taken once a day would be required to combine effective dosages of the combination. The ability to formulate stable beadlets of stavudine in accordance with the present invention enables such combination therapy possible to that effective blood levels of the combination over 24 hours can be realized with a single dosage.

It is understood that various other embodiments and modifications in the practice of the invention will be apparent to, and can be readily made by, those of ordinary skill in the art without departing form the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLE 1

Extended release beadlets were prepared from the following formulation:

| Ingredient | Mg\Capsule |
| --- | --- |
| Core Beads | |
| Stavudine | 37.5 |
| Lactose Hydrous, NF | 8.8 |
| Microcrystalline Cellulose, NF | 5.6 |
| Magnesium Stearate | 0.6 |
| Seal Coat | |
| Hydroxypropyl Methylcellulose, USP | 1.9 |
| Talc, USP | 0.9 |
| Modified Release Coat | |
| Ethylcellulose Aqueous Dispersion, NF (dry weight) | 2.2 |
| Distilled Acetylated Monoglycerides | 0.9 |
| Encapsulation | |
| Hard Gelatin Capsules - fill weight | 68.4 |

Ethylcellulose Aqueous Dispersion, NF utilized as Aquacoat ECD from FMC Corporation, contains ethylcellulose, cetyl alcohol, sodium lauryl sulfate and water. Distilled Acetylated Monoglycerides is manufactured by Eastman chemical Company and contains distilled acetylated monoglycerides, propylene glycol, propyl gallate and citric acid.

The core ingredients were thoroughly mixed and thereafter kneaded in a planetary mixer with sufficient water to form a wet mass. The wet mass was passed through a Nica E140 extruder to form an extrudate approximately 0.8 mm in diameter. The extrudate was then passed through a Caleva spheronizer to form beadlets that were dried at 65° C. for 2 hours in a fluid bed dryer. The dried beadlets were then treated to form a seal coating by spraying with an aqueous solution of hydroxypropyl methylcellulose to which the talc had been added to form a suspension. It was necessary to stir the suspension to prevent the talc from settling. The beadlets were then coated with a barrier coating comprising an aqueous dispersion of ethylcellulose with a plasticizer consisting of distilled acetylated monoglycerides as described above and cured for two hours in an oven. The cured beadlets were filled into gelatin capsules. Analysis of the beadlets showed no appreciable loss of potency of stavudine through hydrolysis resulting from the technique of preparation.

EXAMPLE 2

Extended release beadlets were prepared according to the method of Example 1 from the following formulation.

| Ingredient | Mg\Capsule |
|---|---|
| Core Beads | |
| Stavudine | 100.0 |
| Lactose Hydrous, NF | 23.3 |
| Microcrystalline Cellulose, NF | 41.7 |
| Magnesium Stearate | 1.7 |
| Seal Coat | |
| Hydroxypropyl Methylcellulose, USP | 5.0 |
| Talc, USP | 2.5 |
| Modified Release Coat | |
| Ethylcellulose Aqueous Dispersion, NF (dry weight) | 5.8 |
| Distilled Acetylated Monoglycerides | 2.3 |
| Encapsulation | |
| Hard Gelatin Capsules - fill weight | 182.3 |

Analysis showed no appreciable loss of potency of stavudine from the preparation.

EXAMPLE 3

Mixtures of beadlets of stavudine formed according to the procedure described in Examples 1 and 2 were filled into hard gelatin capsules and similar beadlets containing the antiretroviral medicaments didanosine (2',3'-dioxyinosine) and [3S-(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl }-2,3,6,10,13-pentaazaretetradecanedioic acid dimethyl ester. The formulation of the latter beadlets and the process for preparing them was generally as described in Examples 1 and 2. The beadlets and their content are given in Table 1. The values in each column represent the fill weight of the respective beadlets with the potency of the medicament being given in parenthesis. Therefore, the first value given for Stavudine beadlets is a fill weight of 61 mg. of which 33 mg is stavudine and the remainder excipients. The total fill weight given in the right-hand column represents medicament plus excipients.

TABLE 1

| Capsule Size | Stavudine Beadlets (Potency) | Didanosine Beadlets (Potency) | Beadlets of Example 3 (Potency) | Total Fill Weight in mg |
|---|---|---|---|---|
| 0 | 61 (33) | 178 (133) | 249 (133) | 488 |
| 00 | 61 (33) | 178 (133) | 360 (133) | 599 |
| 1 | 91 (50) | 267 (200) | — | 358 |
| 0 | 137 (75) | 334 (250) | — | 471 |
| 0 | 91 (50) | — | 360 (200) | 451 |

EXAMPLE 4

Beadlets were prepared in accordance with the procedure of Examples 1 and 2 containing in each instance 67% by weight of Stavudine and 10% by weight of microcrystalline cellulose. Formulations containing the following excipients were tested utilizing recognized standards for both Yellowness (ASTM D1925) and Whiteness (Berger 59). The results are given in Table 2.

TABLE 2

| Excipients - By Weight | Yellowness | Whiteness |
|---|---|---|
| Lactose 22% Talc 1% | 17.2 | 6.5 |
| Lactose 21% Silicon Dioxide 2% | 17.3 | 5.9 |
| Lactose 20% Silicon Dioxide 1% Talc 2% | 23.5 | 3.8 |
| Lactose 22% Silicon Dioxide 1% | 12.7 | 8.2 |
| Lactose 23% | 15.6 | 6.5 |
| Lactose 22% Magnesium Stearate 1% | 8.5 | 11.5 |

The data in Table 2 clearly demonstrates that beadlets prepared from the formulations of the present invention have superior color, measured both in terms of Whiteness and lack of Yellowness.

EXAMPLE 5

Beadlets were prepared in accordance with the procedure of Examples 1 and 2 from a formulation containing 60% by weight stavudine, 25% by weight microcrystalline cellulose and 15% by weight lactose. Similar beadlets were prepared in accordance with the present invention wherein 1% by weight of the lactose was replaced with magnesium stearate. The Seal Coat was Opadry (Colorcon) which is comprised of hydroxypropyl methylcellulose and polyethylene glycol. The Modified Release Coat was as described in Examples 1 and 2. The beadlets were stored under controlled conditions of 40° C. and 75% relative humidity. Samples of the beadlets were analyzed for the presence of Thymine at regular intervals. It is recognized that the mechanism of degradation of stavudine is the hydrolysis of the β-glycosidic bond between the N-1 pyrimidine base nitrogen and the carbon of the unsaturated pentose moiety to form thymine and an unsaturated sugar. HPLC detection of thymine is therefore a reliable means of tracking the degradation of stavudine over time since the quantity of thymine detected is a direct correlation to the amount of stavudine degraded. The results are shown in Table 3.

TABLE 3

| Time at 40° C. and 75% RH | Formula without Magnesium Stearate Percent Thymine Detected | Formula with Magnesium Stearate Percent Thymine Detected |
|---|---|---|
| Initial | 0.24 | 0.14 |
| One month | 0.37 | 0.20 |
| Two months | 0.43 | 0.31 |
| Three months | 0.52 | 0.27 |
| Six months | 0.88 | 0.38 |

The data in Table 3 clearly demonstrates the unexpected stabilizing effect of magnesium stearate in the formulations of the present invention in preventing degradation of stavudine.

We claim:

1. Extruded-spheronized beadlets comprising stavudine, a spheronizing agent, and a quantity of magnesium stearate sufficient to stabilize stavudine against degradation during the extrusion-spheronization process.

2. The beadlets of claim 1 containing from about 0.5 to about 3.0 percent by weight of magnesium stearate based on the weight of stavudine present therein.

3. The beadlets of claim 1 containing from about 1.4 to about 1.7 percent by weight of magnesium stearate based on the weight of stavudine present therein.

4. The beadlets of claim 1 wherein the spheronizing agent is selected from the group consisting of microcrystalline cellulose, sodium carboxymethyl cellulose and corn starch.

5. The beadlets in claim 4 wherein the spheronizing agent is microcrystalline cellulose.

6. The beadlets of claim 1, further comprising a diluent.

7. The beadlets of claim 6 wherein said diluent is selected from consisting of lactose, dicalcium phosphate, mannitol and cornstarch.

8. The beadlets of claim 1, further comprising a seal coating and a modified release coating.

9. The beadlets of claim 8 wherein the seal coating comprises a film-former and an antiadherent, and the modified release coating comprises a polymeric barrier material and a plasticizer therefor.

10. The beadlets of claim 9 wherein the film-former is selected from the group consisting of hydroxypropyl methylcellulose and hydroxypropyl cellulose.

11. The beadlets of claim 9 wherein the antiadherent is selected from the group consisting of talc, microcrystalline cellulose and magnesium stearate.

12. The beadlets of claim 9 wherein the polymeric barrier material comprises polymethacrylate.

13. The beadlets of claim 9 wherein the polymeric barrier material comprises ethylcellulose.

14. The beadlets of claim 9 wherein the plasticizer comprises acylated monoglycerides.

15. Extended-sphereonized beadlets, comprising:
    a) stavudine;
    b) a spheronizing agent;
    c) a diluent;
    d) magnesium stearate in an amount sufficient to stabilize stavudine against degradation during the extrusion-spheronization process;
    e) a seal coating; and
    f) a modified release coating.

16. The beadlets of claim 15 containing from about 33 to about 67 percent by weight of stavudine.

17. The beadlets of claim 15 wherein the spheronizing agent is selected from the group consisting of microcrystalline cellulose, sodium carboxymethyl cellulose and corn starch.

18. The beadlets of claim 15 wherein the diluent is selected from the group consisting of lactose, dicalcium phosphate, manitol and corn starch.

19. The beadlets of claim 15 wherein
    a) the spheronizng agent is microcrystalline cellulose;
    b) the diluent is lactose;
    c) the seal coating comprises a film-former and an antiadherent; and
    d) the modified release coating comprises a polymeric barrier material and a plasticizer.

20. The beadlets of claim 19 wherein said film-former is hydroxypropyl methylcellulose, said antiadherent is talc, said polymeric barrier material is ethylcellulose and said plasticizer comprises distilled acetylated monoglycerides.

21. A pharmaceutical dosage form comprising a hard gelatin capsule containing a sufficient amount of the beadlets of claim 1, 15 or 19 to provide an effective dosage of stavudine over approximately 24 hours.

22. The pharmaceutical dosage form of claim 21, wherein said capsule additionally contains beadlets containing at least one other medicament useful in treating retroviral infections such that blood levels of said other medicament are provided over approximately 24 hours.

23. A pharmaceutical dosage form of claim 22, wherein said other medicaments are selected from the group consisting of didanosine, [3S-(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl }-2,3,6,10,13-pentaazaretetradecanedioic acid dimethyl ester, indinavir and lodenosine.

24. The pharmaceutical dosage form of claim 23 wherein said other medicament is didanosine.

25. The pharmaceutical dosage form of claim 23 wherein said other medicament comprises
    (a) [3S-(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl }-2,3,6,10,13-pentaazaretetradecanedioic acid dimethyl ester; and
    (b) optionally didanosine.

26. A method of treating a patient in need of therapy for a retroviral infection comprising administering to said patient a pharmaceutical dosage form comprising a hard gelatin capsule containing a sufficient amount of the beadlets of claim 1, 15 or 19 to provide an effective dosage of stavudine, thereby providing said treatment over approximately 24 hours.

27. The method of claim 26 wherein said capsule additionally contains beadlets containing at least one other medicament useful in treating retroviral infections such that treatment with said other medicament is provided over approximately 24 hours.

28. The method of claim 27 wherein said other medicament is selected from the group consisting of didanosine, [3S -(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl }-2,3,6,10,13-pentaazaretetradecanedioic acid dimethyl ester, indinavir and lodenosine.

29. The method of claim 28 wherein said other medicament is at least one of didanosine and [3S-(3R*,8R*,9R*, 12R*)]-3,12-Bis(1,1-dimethylethyl)-8-hydroxy-4,11-dioxo-9-(phenylmethyl)-6{[4-(2-pyridinyl)phenyl]methyl }-2,3,6, 10,13-pentaazaretetradecanedioic acid dimethyl ester.

30. The method of claim 29 wherein said other medicament is didanosine.

31. A process of forming beadlets containing stavudine, comprising:
    (a) forming a wet mass of stavudine, a spheronizing agent, an optional diluent, an amount of magnesium stearate sufficient to stabilize the stavudine against degradation during said process, and water sufficient to form a wet mass suitable for extrusion;
    (b) extruding said mass to form an extrudate;
    (c) spheronizing said extrudate to form beadlets; and
    (d) drying said beadlets.

32. The process of claim 31, further comprising the steps of forming a seal coating over said beadlets and forming a modified release coating over said seal coating.

33. The process of claim 32 wherein said spheronizing agent is microcrystalline cellulose, said diluent is lactose, said seal coating comprises a film-former and an antiadherent, and said modified release coating comprises a polymeric barrier material and a plasticizer therefor.

34. The process of claim 31, further comprising the step of blending stavudine, the spheronizing agent, the optional diluent and magnesium stearate prior to forming the wet mass.

* * * * *

UNITED STATES PATENT AND TRADEMARK OFFICE
CERTIFICATE OF CORRECTION

| | |
|---|---|
| PATENT NO. | : 7,135,465 B2 |
| APPLICATION NO. | : 09/821103 |
| DATED | : November 14, 2006 |
| INVENTOR(S) | : Robert Abramowitz, Denise M. O'Donoghue and Nemichand B. Jain |

Page 1 of 1

It is certified that error appears in the above-identified patent and that said Letters Patent is hereby corrected as shown below:

Column 9:
Claim 7, line 11, "from consisting of" should be --from the group consisting of--.

Column 9:
Claim 15, line 31, "Extended-sphereonized beadlets" should be --Extruded-spheronized beadlets--.

Signed and Sealed this

Eighteenth Day of September, 2007

JON W. DUDAS
*Director of the United States Patent and Trademark Office*